US009302109B2

(12) United States Patent
Sabesan

(10) Patent No.: US 9,302,109 B2
(45) Date of Patent: Apr. 5, 2016

(54) CRANIAL NERVE STIMULATION TO TREAT DEPRESSION DURING SLEEP

(71) Applicant: CYBERONICS, INC., Houston, TX (US)

(72) Inventor: Shivkumar Sabesan, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 0 days.

(21) Appl. No.: 14/262,508

(22) Filed: Apr. 25, 2014

(65) Prior Publication Data
US 2015/0306392 A1    Oct. 29, 2015

(51) Int. Cl.
| A61N 1/00 | (2006.01) |
| A61N 1/36 | (2006.01) |
| A61B 5/0402 | (2006.01) |
| A61B 5/0476 | (2006.01) |
| A61B 5/0488 | (2006.01) |
| A61B 5/0496 | (2006.01) |
| A61B 5/11 | (2006.01) |
| A61B 5/00 | (2006.01) |
| A61N 1/05 | (2006.01) |

(52) U.S. Cl.
CPC .......... *A61N 1/36096* (2013.01); *A61B 5/0402* (2013.01); *A61B 5/0476* (2013.01); *A61B 5/0488* (2013.01); *A61B 5/0496* (2013.01); *A61B 5/11* (2013.01); *A61B 5/4806* (2013.01); *A61B 5/4812* (2013.01); *A61N 1/0529* (2013.01); *A61N 1/36082* (2013.01); *A61N 1/36135* (2013.01)

(58) Field of Classification Search
CPC ..................................................... A61N 1/3605
USPC ..................................................... 607/2, 9, 45
See application file for complete search history.

(56) References Cited

U.S. PATENT DOCUMENTS

| 4,702,254 A | 10/1987 | Zabara |
| 4,867,164 A | 9/1989 | Zabara |
| 4,920,979 A | 5/1990 | Bullara |
| 4,979,511 A | 12/1990 | Terry, Jr. |
| 5,012,411 A | 4/1991 | Policastro et al. |
| 5,025,807 A | 6/1991 | Zabara |
| 5,081,987 A | 1/1992 | Nigam |
| 5,137,020 A | 8/1992 | Wayne et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |

(Continued)

OTHER PUBLICATIONS

International Application No. PCT/US2015/024960, "PCT Search Report and Written Opinion" dated Jun. 17, 2015, 12 pages, Rijswijk and Munich.
Borovikova, L.V. et al., "Vagus Nerve Stimulation Attenuates the Systemic Inflammatory Response to Endotoxin," Letters to Nature, Nature, vol. 405, May 25, 2000, pp. 458-462.

(Continued)

*Primary Examiner* — Nicole F. Lavert
*Assistant Examiner* — Nadia A Mahmood
(74) *Attorney, Agent, or Firm* — Foley & Lardner LLP

(57) ABSTRACT

A method includes determining sleep cycle information related to a sleep cycle of a patient based on body parameter data. The method also includes adjusting a cranial nerve stimulation parameter based on the sleep cycle information. The method further includes applying a cranial nerve stimulation therapy to treat depression based on the adjusted cranial nerve stimulation parameter.

20 Claims, 7 Drawing Sheets

(56) References Cited

U.S. PATENT DOCUMENTS

| | | |
|---|---|---|
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A * | 8/1994 | Terry et al. ............... 607/45 |
| 5,458,625 A | 10/1995 | Kendall |
| 5,522,862 A | 6/1996 | Testerman et al. |
| 5,531,778 A | 7/1996 | Maschino et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,435 A | 2/1997 | Quy |
| 5,611,350 A | 3/1997 | John |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,720,771 A | 2/1998 | Snell |
| 5,743,860 A | 4/1998 | Hively et al. |
| 5,814,092 A | 9/1998 | King |
| 5,913,882 A | 6/1999 | King |
| 5,916,239 A | 6/1999 | Geddes et al. |
| 5,928,272 A | 7/1999 | Adkins et al. |
| 5,995,868 A | 11/1999 | Dorfmeister et al. |
| 6,016,449 A | 1/2000 | Fischell et al. |
| 6,018,682 A | 1/2000 | Rise |
| 6,041,258 A | 3/2000 | Cigaina et al. |
| 6,061,593 A | 5/2000 | Fischell et al. |
| 6,073,048 A | 6/2000 | Kieval et al. |
| 6,104,956 A | 8/2000 | Naritoku et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,240,316 B1 | 5/2001 | Richmond et al. |
| 6,269,270 B1 | 7/2001 | Boveja |
| 6,304,775 B1 | 10/2001 | Iasemidis et al. |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,788 B2 | 3/2002 | Boveja |
| 6,366,814 B1 | 4/2002 | Boveja et al. |
| 6,459,936 B2 | 10/2002 | Fischell et al. |
| 6,473,639 B1 | 10/2002 | Fischell et al. |
| 6,473,644 B1 | 10/2002 | Terry, Jr. et al. |
| 6,484,132 B1 | 11/2002 | Hively et al. |
| 6,505,074 B2 | 1/2003 | Boveja et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,606,523 B1 | 8/2003 | Jenkins |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,658,294 B1 | 12/2003 | Zadeh et al. |
| 6,662,052 B1 | 12/2003 | Sarwal et al. |
| 6,668,191 B1 | 12/2003 | Boveja |
| 6,671,555 B2 | 12/2003 | Gielen et al. |
| 6,671,556 B2 | 12/2003 | Osorio et al. |
| 6,681,003 B2 | 1/2004 | Linder et al. |
| 6,684,104 B2 | 1/2004 | Gordon et al. |
| 6,684,105 B2 | 1/2004 | Cohen et al. |
| 6,708,064 B2 | 3/2004 | Rezai |
| 6,721,603 B2 | 4/2004 | Zabara et al. |
| 6,760,626 B1 | 7/2004 | Boveja |
| 6,764,498 B2 | 7/2004 | Mische |
| 6,768,969 B1 | 7/2004 | Nikitin et al. |
| 6,819,956 B2 | 11/2004 | DiLorenzo |
| 6,904,390 B2 | 6/2005 | Nikitin et al. |
| 6,920,357 B2 | 7/2005 | Osorio et al. |
| 6,922,592 B2 | 7/2005 | Thompson et al. |
| 6,934,580 B1 | 8/2005 | Osorio et al. |
| 6,944,501 B1 | 9/2005 | Pless |
| 6,959,215 B2 | 10/2005 | Gliner et al. |
| 6,961,618 B2 | 11/2005 | Osorio et al. |
| 7,006,872 B2 | 2/2006 | Gielen et al. |
| 7,043,305 B2 | 5/2006 | KenKnight et al. |
| 7,050,856 B2 | 5/2006 | Stypulkowski |
| 7,054,792 B2 | 5/2006 | Frei et al. |
| 7,076,288 B2 | 7/2006 | Skinner |
| 7,079,977 B2 | 7/2006 | Osorio et al. |
| 7,134,996 B2 | 11/2006 | Bardy |
| 7,146,211 B2 | 12/2006 | Frei et al. |
| 7,149,572 B2 | 12/2006 | Frei et al. |
| 7,149,581 B2 | 12/2006 | Goedeke |
| 7,156,808 B2 | 1/2007 | Quy |
| 7,156,809 B2 | 1/2007 | Quy |
| 7,164,941 B2 | 1/2007 | Misczynski et al. |
| 7,167,743 B2 | 1/2007 | Heruth et al. |
| 7,167,750 B2 | 1/2007 | Knudson et al. |
| 7,171,271 B2 | 1/2007 | Koh et al. |
| 7,188,053 B2 | 3/2007 | Nikitin et al. |
| 7,228,167 B2 | 6/2007 | Kara et al. |
| 7,231,254 B2 | 6/2007 | DiLorenzo |
| 7,236,831 B2 | 6/2007 | Firlik et al. |
| 7,242,983 B2 | 7/2007 | Frei et al. |
| 7,254,439 B2 | 8/2007 | Misczynski et al. |
| 7,263,467 B2 | 8/2007 | Sackellares et al. |
| 7,265,676 B2 | 9/2007 | Gordon et al. |
| 7,277,758 B2 | 10/2007 | DiLorenzo |
| 7,280,867 B2 | 10/2007 | Frei et al. |
| 7,282,030 B2 | 10/2007 | Frei et al. |
| 7,292,890 B2 | 11/2007 | Whitehurst et al. |
| 7,295,881 B2 | 11/2007 | Cohen et al. |
| 7,305,268 B2 | 12/2007 | Gliner et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,340,302 B1 | 3/2008 | Falkenberg et al. |
| 7,353,064 B2 | 4/2008 | Gliner et al. |
| 7,366,572 B2 | 4/2008 | Heruth et al. |
| 7,373,199 B2 | 5/2008 | Sackellares et al. |
| 7,389,144 B1 | 6/2008 | Osorio et al. |
| 7,401,008 B2 | 7/2008 | Frei et al. |
| 7,403,820 B2 | 7/2008 | DiLorenzo |
| 7,483,747 B2 | 1/2009 | Gliner et al. |
| 7,894,890 B2 | 2/2011 | Sun et al. |
| 2002/0072782 A1 | 6/2002 | Osorio et al. |
| 2002/0099417 A1 | 7/2002 | Naritoku et al. |
| 2002/0151939 A1 | 10/2002 | Rezai |
| 2002/0188214 A1 | 12/2002 | Misczynski et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138647 A1 | 7/2004 | Osorio et al. |
| 2004/0138711 A1 | 7/2004 | Osorio et al. |
| 2004/0158119 A1 | 8/2004 | Osorio et al. |
| 2004/0199212 A1 | 10/2004 | Fischell et al. |
| 2005/0124901 A1 | 6/2005 | Misczynski et al. |
| 2005/0143786 A1 | 6/2005 | Boveja |
| 2005/0148893 A1 | 7/2005 | Misczynski et al. |
| 2005/0148895 A1 | 7/2005 | Misczynski et al. |
| 2005/0154425 A1 | 7/2005 | Boveja et al. |
| 2005/0177192 A1 | 8/2005 | Rezai et al. |
| 2005/0187590 A1 | 8/2005 | Boveja et al. |
| 2005/0187796 A1 | 8/2005 | Rosenfeld et al. |
| 2005/0192644 A1 | 9/2005 | Boveja et al. |

(56) References Cited

U.S. PATENT DOCUMENTS

| | | |
|---|---|---|
| 2005/0197590 A1 | 9/2005 | Osorio et al. |
| 2005/0277998 A1 | 12/2005 | Tracey et al. |
| 2006/0009815 A1 | 1/2006 | Boveja et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong |
| 2007/0088404 A1 | 4/2007 | Wyler et al. |
| 2007/0100278 A1 | 5/2007 | Frei et al. |
| 2007/0100392 A1 | 5/2007 | Maschino et al. |
| 2007/0123758 A1 | 5/2007 | Miesel et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0239210 A1 | 10/2007 | Libbus et al. |
| 2007/0244407 A1 | 10/2007 | Osorio |
| 2007/0282177 A1 | 12/2007 | Pilz |
| 2008/0033508 A1 | 2/2008 | Frei et al. |
| 2008/0064934 A1 | 3/2008 | Frei et al. |
| 2008/0071327 A1 | 3/2008 | Miesel et al. |
| 2008/0081941 A1 | 4/2008 | Tononi |
| 2008/0103548 A1 | 5/2008 | Fowler et al. |
| 2008/0119900 A1 | 5/2008 | DiLorenzo |
| 2008/0195166 A1 | 8/2008 | Sun et al. |
| 2008/0208285 A1 | 8/2008 | Fowler et al. |
| 2008/0234598 A1 | 9/2008 | Snyder et al. |
| 2008/0234785 A1 | 9/2008 | Nakayama et al. |
| 2009/0198145 A1 | 8/2009 | Chow |
| 2010/0087701 A1* | 4/2010 | Berka et al. ............ 600/27 |
| 2011/0029044 A1 | 2/2011 | Hyde et al. |
| 2011/0112381 A1 | 5/2011 | Sun et al. |
| 2011/0295083 A1 | 12/2011 | Doelling et al. |
| 2012/0277618 A1 | 11/2012 | Giftakis et al. |

OTHER PUBLICATIONS

Chakravarthy, N. et al., "Controlling Synchronization in a Neuron-Level Population Model," International Journal of Neural Systems, vol. 17, No. 2, 2007, pp. 123-138.

Chen, C. et al., "Vagal Efferent Fiber Stimulation Ameliorates Pulmonary Microvascular Endothelial Cell Injury by Downregulating Inflammatory Responses," Inflammation, vol. 36, No. 6, Dec. 2013, pp. 1567-1575.

Dodrill, C.B. et al., "Effects of Vagal Nerve Stimulation on Cognition and Quality of Life in Epilepsy," Epilepsy & Behavior, vol. 2, Issue 1, 2001, pp. 46-53.

Frei, M.G. et al., "Left Vagus Nerve Stimulation with the Neurocybernetic Prosthesis Has Complex Effects on Heart Rate and on Its Variability in Humans," Epilepsia, vol. 42, No. 8, 2001, pp. 1007-1016.

Iasemidis, L.D. et al., "Spatiotemporal Transition to Epileptic Seizures: A Nonlinear Dynamical Analysis of Scalp and Intracranial EEG Recordings," Spatiotemporal Models in Biological and Artificial Systems, IOS Press, 1997, pp. 81-88.

Jaseja, H., "Vagal Nerve Stimulation Technique: Enhancing Its Efficacy and Acceptability by Augmentation with Auto Activation and Deactivation Mode of Operation," Medical Hypotheses, vol. 63, Issue 1, 2004, pp. 76-79.

Kucera, M., "'Active Air' Inhalation Therapy: Autonomic Regulation Mechanisms with Use of Heart Rate Variability Analysis," Explore! vol. 16, No. 2, 2007, 3 pages.

Malow, B.A. et al., "Vagus Nerve Stimulation Reduces Daytime Sleepiness in Epilepsy Patients," Neurology, vol. 57, Issue 5, 2001, pp. 879-884.

Valdes-Cruz, A. et al., "Chronic Stimulation of the Cat Vagus Nerve Effect on Sleep and Behavior," Progress in Neuro-Psychopharmacology & Biological Psychiatry, vol. 26, Issue 1, 2002, pp. 113-118.

Zabara, J., "Neuroinhibition in the Regulation of Emesis," Space Life Sciences, vol. 3, Issue 3, 1972, pp. 282-292.

* cited by examiner

CRANIAL NERVE STIMULATION TO TREAT DEPRESSION DURING SLEEP

RELATED APPLICATIONS

This application is related to U.S. patent application Ser. No. 13/834,523, filed Mar. 15, 2013, entitled "Optimization of Cranial Nerve Stimulation to Treat Seizure Disorders During Sleep," which is hereby incorporated by reference as though fully set forth herein. This application is also related to U.S. patent application Ser. No. 14/262,449, filed Apr. 25, 2014, entitled "Detecting Seizures Based on Heartbeat Data," and is hereby incorporated by reference as though fully set forth herein.

FIELD OF THE DISCLOSURE

The present disclosure is generally related to cranial nerve stimulation to treat depression.

BACKGROUND

The human nervous system includes the brain and the spinal cord, collectively known as the central nervous system. The central nervous system includes nerve fibers that transmit nerve signals to, from, and within the brain and spinal cord. The network of nerves in the remaining portions of the human body forms the peripheral nervous system. A system of peripheral nerves connects directly to the brain to control various brain functions, such as vision, eye movement, hearing, facial movement, and feeling. Another system of peripheral nerves, known as the autonomic nervous system, controls autonomic functions. Autonomic functions include blood pressure, body temperature, heartbeat, blood vessel diameter control, intestinal movements, actions of many internal organs, and other body activities and functions that occur without voluntary control.

Neurological disorders may affect the human nervous system. Some neurological disorders may be treated with medication, with neurostimulation, or both. Neurostimulation may include electrical stimulation of the nervous system. An example of a neurological disorder is depression.

SUMMARY

Efficacy of depression treating therapy may be difficult to quantify. Systems and methods described herein may determine efficacy of a therapy for treating depression and may treat depression during sleep.

For example, an implantable medical device (IMD) may determine sleep cycle information related to one or more sleep cycles of a patient (e.g., a patient diagnosed with depression) by monitoring body parameter data of the patient. The sleep cycle information may include a particular sleep stage, a sleep stage transition, an amount of time the patient spent in one or more sleep stages during a sleep cycle and/or multiple sleep cycles, or a combination thereof. The IMD may adjust one or more CNS parameters of a CNS therapy based on the sleep cycle information to treat depression. Based on the sleep cycle information, the IMD may also, or in the alternative, determine information regarding efficacy of the CNS therapy. The IMD may also, or in the alternative, adjust the one or more CNS parameters based on the information regarding efficacy to adjust the CNS therapy. CNS may include vagus nerve stimulation (VNS), trigeminal nerve stimulation (TNS), stimulation of other cranial nerves, or a combination thereof.

To illustrate, the IMD may determine a sleep stage and may monitor sleep stage transitions. Based on the sleep stage, the IMD may adjust the one or more CNS parameters of the CNS therapy. Based on the adjusted one or more CNS parameters, the IMD may apply a CNS therapy to drive the patient toward the next sleep stage (e.g., from stage 1 sleep to stage 2 sleep, from stage 2 sleep to stage 3 sleep, from stage 3 sleep to rapid eye movement (REM) stage sleep, from REM stage sleep to stage 1 sleep) to enable the patient to receive an amount of REM stage sleep time that is greater than or equal to a threshold. An amount of time that the patient spends in REM stage sleep is associated with serotonin production of the patient. Increasing the amount of time spent in REM stage sleep may increase the production of serotonin within the patient. An increased amount of serotonin production within the patient may reduce a depressive state of the patient (e.g., the patient may feel less depressed).

The IMD may also, or in the alternative, determine information regarding efficacy of a therapy for treating depression based on the sleep cycle information. For example, the IMD or an external device (e.g., a computing device) may compute an amount of time the patient spends in REM stage sleep before applying therapy based on the sleep cycle information. The IMD or the external device may compute an amount of time the patient spends in REM stage sleep during and/or after the therapy. The IMD may compare sleep cycle information (e.g., REM stage sleep time) of the patient before applying the therapy to sleep cycle information of the patient during and/or after during the therapy. One or more parameters of the therapy may be adjusted based on the comparison to increase the efficacy of the therapy.

In a particular embodiment, a method includes determining sleep cycle information related to a sleep cycle of a patient based on body parameter data. The method also includes adjusting a cranial nerve stimulation parameter based on the sleep cycle information. The method further includes applying a cranial nerve stimulation therapy to treat depression based on the adjusted cranial nerve stimulation parameter.

In another particular embodiment, a device includes a processor that is configured to determine sleep cycle information related to a sleep cycle of a patient based on body parameter data. The processor is also configured to adjust a cranial nerve stimulation parameter based on the sleep cycle information. The processor is further configured to apply a cranial nerve stimulation therapy to treat one or more depression based on the adjusted cranial nerve stimulation parameter. The apparatus also includes a memory coupled to the processor.

In another particular embodiment, a non-transitory computer-readable medium includes instructions executable by a processor. The instructions may be executable by the processor to determine sleep cycle information related to a sleep cycle of a patient based on body parameter data. The instructions may also be executable by the processor to adjust a cranial nerve stimulation parameter based on the sleep cycle information. The instructions may further be executable by the processor to apply a cranial nerve stimulation therapy to treat depression based on the adjusted cranial nerve stimulation parameter.

DETAILED DESCRIPTION

Figure 1:
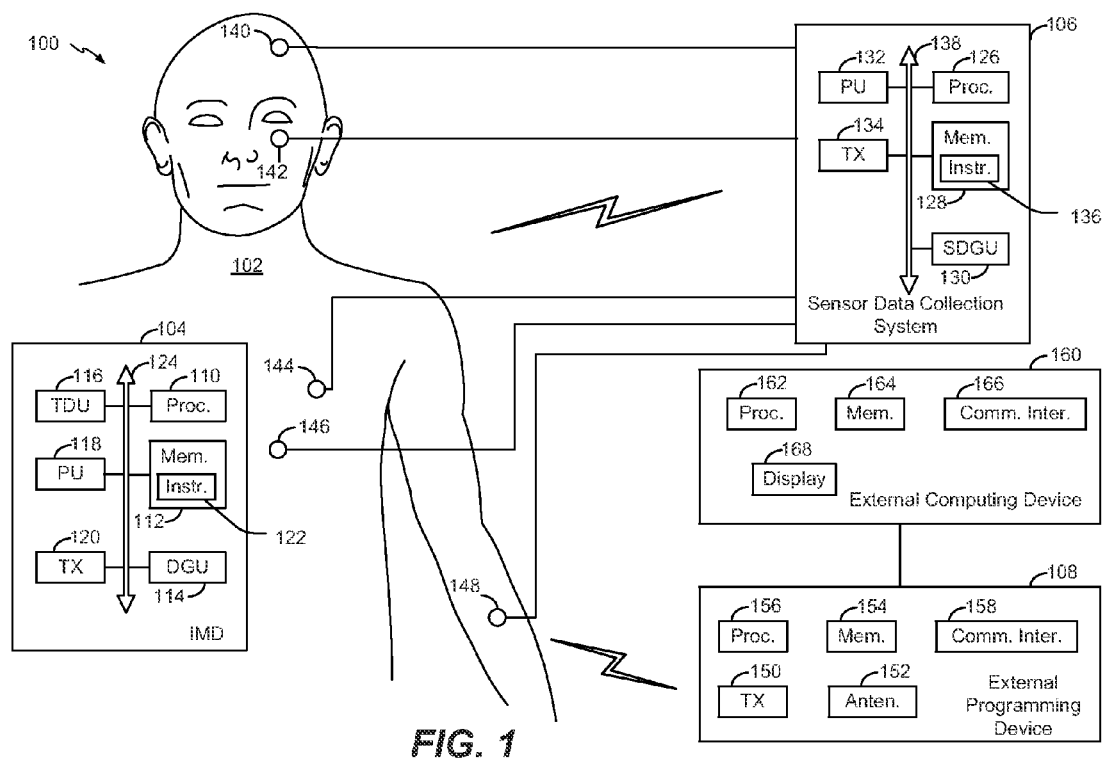
FIG. 1 is a block diagram of a particular embodiment of a system that uses cranial nerve stimulation to treat depression during sleep.

Referring to FIG. 1, a block diagram of a system 100 that uses cranial nerve stimulation (CNS) to treat depression of a patient 102 (e.g., a patient diagnosed with depression) during sleep is shown according to an exemplary embodiment. CNS may include vagus nerve stimulation (VNS), trigeminal nerve stimulation (TNS), stimulation of other cranial nerves, or a combination thereof. The system 100 may include an implantable medical device (IMD) 104, a sensor data collection system 106, and/or an external programming device 108. The IMD 104 may include a processor 110, a memory 112, a data gathering unit (DGU) 114, a therapy delivery unit (TDU) 116, a power unit (PU) 118, a transceiver (TX) 120, a system bus 124, other components (not shown), or a combination thereof. The processor 110 may be a single processor of the IMD 104 or multiple processors of the IMD 104. The memory 112 may include instructions 122 that are executable by the processor 110 to perform or control various functions of the IMD 104.

The data gathering unit 114 may gather data related to an operational state of the IMD 104 (e.g., a charge state of the power unit 118), data related to therapy provided to the patient 102, body parameter data corresponding to one or more body parameters of the patient 102, or a combination thereof. Data gathered by the data gathering unit 114 may be used to control therapy provided to the patient 102, may be transmitted to an external device, may be stored in the memory 112, transmitted to a server (e.g., a cloud), or a combination thereof.

The therapy delivery unit 116 may be configured to provide therapy to the patient 102. For example, the therapy delivery unit 116 may provide electrical stimulation (via one or more electrodes (not shown)) to tissue of the patient 102. The therapy delivery unit 116 may provide electrical stimulation to a cranial nerve (e.g., the vagus nerve, the trigeminal nerve, etc.) of the patient 102. As another example, the therapy delivery unit 116 may include a drug pump that delivers a drug or drugs to the patient 102. Therapy provided by the therapy delivery unit 116 may be controlled by the processor 110 based on a treatment program.

The power unit 118 may provide electrical power to components of the IMD 104. For example, the power unit 118 may include a battery or a capacitor. The transceiver 120 may enable the IMD 104 to communicate with other devices, such as the sensor data collection system 106 and the external programming device 108. The processor 110, the memory 112, the data gathering unit 114, the therapy delivery unit 116, the power storage unit 118, the transceiver 120, other components of the IMD 104, or a combination thereof, may be connected via the system bus 124.

The sensor data collection system 106 may include a processor 126, a memory 128, a sensor data gathering unit (SDGU) 130, a power unit (PU) 132, a transceiver (TX) 134, a system bus 138, other components (not shown), or a combination thereof. The processor 126 may be a single processor of the sensor data collection system 106 or multiple processors of the sensor data collection system 106. The memory 128 may include instructions 136 that are executable by the processor 126 to perform or control various functions of the sensor data collection system 106.

The sensor data gathering unit 130 may be configured to collect body parameter data from sensors placed on or implanted within tissue of the patient 102. For example, an electroencephalography (EEG) sensor 140, an electrooculography (EOG) sensor 142, an electrocardiography (ECG) sensor 144, an electromyography (EMG) sensor 146, an accelerometer 148 (disposed on a limb as illustrated in FIG. 1 or disposed elsewhere on the body, such as on the torso or head as shown for sensors 140, 142, 144, and 146), an impedance monitoring unit, a respiration sensor (e.g., on the chest or nose), a blood oxygenation sensor, an acoustic sensor (e.g., to measure snoring), other sensors, or a combination thereof, may be placed on the surface of the skin or implanted within tissue of the patient 102 to sense the body parameter data of the patient 102. The body parameter data may include EEG data, EOG data, ECG data, EMG data, accelerometer data, or a combination thereof. The sensor data gathering unit 130 may receive the body parameter data via respective wired or wireless connections to the EEG sensor 140, the EOG sensor 142, the ECG sensor 144, the EMG sensor 146, the accelerometer 148, the respiration sensor, the other sensors described above, or a combination thereof.

The power unit 132 may be configured to provide electrical power to components of the sensor data collection system 106. For example, the power unit 132 may include a battery, a capacitor, a power supply coupled to an external source (e.g., alternate current (AC) power), or a combination thereof. The power unit 132 may be configured to selectively power on and off one or more of the various sensors on demand. The transceiver 134 may be configured to enable the sensor data collection system 106 to communicate with other devices, such as the IMD 104, the external programming device 108, or both. The processor 126, the memory 128, the sensor data gathering unit 130, the power unit 132, and the transceiver 134 may be connected via the system bus 138.

The external programming device 108 may include a transceiver (TX) 150 and an antenna 152. The transceiver 150 may be configured to communicate (e.g., transmit data, receive data, or a combination thereof) via the antenna 152 with the IMD 104, the sensor data collection system 106, or both. For example, the external programming device 108 may send program data, such as therapy parameter data to the IMD 104 using wireless signals. The program data may be stored at a memory 154 of the external programming device 108, may be received from an external computing device 160, or both. In a particular embodiment, the external programming device 108 may also include a processor 156 and/or a communication interface 158 to communicate with the external computing device 160.

The external computing device 160 may include a processor 162, a memory 164, a communication interface 166, a display 168, other components (not shown), or a combination thereof. The external computing device 160 may receive data from the external programming device 108, the sensor data collection system 106, the IMD 104, or a combination thereof, via the communication interface 166 and may store the data in the memory 164. The external computing device 160 may provide an interface (e.g., via the display 168) to the patient 102 and/or a health care provider to see the stored data. The stored data may be used to facilitate determining information regarding efficacy of a therapy.

During operation, when the patient 102 is asleep, the sensor data collection system 106 may collect the body parameter data from the EEG sensor 140, the EOG sensor 142, the ECG sensor 144, the EMG sensor 146, the accelerometer 148, another sensor, or a combination thereof. The sensor data collection system 106 may communicate the body parameter data to the IMD 104 occasionally (e.g., periodically or in response to detection of an event) or continuously. For example, the sensor data collection system 106 may communicate the body parameter data to the IMD 104 in real time (as soon as the sensor data collection system 106 receives the body parameter data and processes the body parameter data for transmission). Based on the body parameter data, the IMD 104, the sensor data collection system 106, the external programming device 108, the external computing device 160, or a combination thereof, may determine sleep cycle information related to a sleep cycle of the patient 102.

The IMD 104, the sensor data collection system 106, the external programming device 108, the external computing device 160, or a combination thereof, may evaluate the sleep cycle information to determine a sleep stage (e.g., stage 1 sleep, stage 2 sleep, stage 3 sleep, and/or REM stage sleep) of the patient 102. The IMD 104, the sensor data collection system 106, the external programming device 108, the external computing device 160, or a combination thereof, may also, or in the alternative, evaluate the sleep cycle information to detect a sleep stage transition. For example, the sleep stage transition may include a transition from stage 1 sleep to stage 2 sleep, a transition from stage 2 sleep to stage 3 sleep, a transition from stage 3 sleep to REM stage sleep, a transition from REM stage sleep to stage 1 sleep, a transition from one of stage 1 sleep, stage 2 sleep, stage 3 sleep, and/or REM stage sleep to wakefulness, or a combination thereof.

The IMD 104, the sensor data collection system 106, the external programming device 108, the external computing device 160, or a combination thereof, may also, or in the alternative, evaluate the sleep cycle information to determine an amount of time the patient 102 spends in one or more sleep stages during a sleep cycle (e.g., a sleep quota). The IMD 104, the sensor data collection system 106, the external programming device 108, the external computing device 160, or a combination thereof, may also, or in the alternative, evaluate the sleep cycle information to determine an amount of time the patient 102 has spent in one or more sleeps stages during a sleep period. The sleep period may include multiple sleep cycles. For example, based on body parameter data, the IMD 104, the sensor data collection system 106, the external programming device 108, the external computing device 160, or a combination thereof, may monitor the sleep quota and/or the amount of time the patient 102 has spent in one or more sleep stages during the sleep period.

Based on the sleep cycle information, the IMD 104, the sensor data collection system 106, the external programming device 108, the external computing device 160, or a combination thereof, may adjust one or more cranial nerve stimulation (CNS) parameters to adjust the CNS applied to the patient 102. The one or more CNS parameters may include a pulse width, an output current, an output voltage, a pulse frequency, a burst frequency, an interburst interval, a duty cycle, an on-time, an off-time, a frequency sweep, other signal parameter, or a combination thereof. The one or more CNS parameters may be used to generate stimulation signals applied to a cranial nerve of the patient 102. For example, when the sleep cycle information indicates a transition from stage 2 sleep toward stage 3 sleep, the IMD 104 may adjust the CNS parameter such that synchrony of brainwaves of the patient 102 is decreased so that the CNS may drive the patient toward REM stage. In some embodiments, the IMD 104 may adjust the CNS parameter such that the CNS may drive the patient 102 toward REM stage sleep when the sleep cycle information indicates a transition from stage 2 sleep to stage 3 sleep, a current sleep stage is stage 3 sleep, a predetermined amount of time has been spent in stage 3 sleep during a sleep cycle, or a combination thereof. Applying CNS to drive the patient 102 toward REM stage sleep may enable the patient to complete the sleep cycle. Thus, the patient may receive more REM stage sleep as compared to being awakened. Furthermore, the patient 102 may have improved sleep quality as the patient 102 continues to sleep instead of waking up. Adjusting the CNS parameter such that synchrony of the brainwaves of the patient 102 is either increased or decreased is described in more detail with reference to FIG. 4.

Patients with neurological disorders, including depression, often exhibit poor sleep architecture (e.g., may not spend sufficient time in certain sleep stages). Poor sleep architecture may be a result of the depression, cause the depression, contribute to the depression, worsen the depression, or a combination thereof. In some embodiments, one or more CNS parameters may be adjusted based on the sleep cycle information to improve sleep architecture. For example, the CNS parameters may be adjusted to affect the amount of time spent in the various sleep stages. CNS parameters may be adjusted to drive the patient towards the next sleep stage when the sleep cycle information indicates that too much time is being spent in a particular sleep stage (on average, during a cycle, or a combination thereof), too little time is being spent in a particular sleep stage (on average, during a cycle, or a combination thereof), when a particular transition is detected from one sleep stage to another, based on a current sleep stage, when a particular amount of time has passed in the current sleep stage, based on one or more thresholds associated with one or more sleep stages (e.g., minimum amount of time that should be spent in a particular sleep stage or a fraction thereof), or a combination thereof. The sleep cycle information may be continuously, periodically, or trigger (e.g., based on detection of an event) updated to provide a closed loop system for adjusting the CNS parameters to adjust stimulation based on changes in the patient's sleep cycle. Improved sleep architecture may reduce the depression, substantially reduce the depression, improve other factors contributing to the depression, or a combination thereof.

As another example, when the sleep cycle information indicates that an amount of time the patient 102 has spent in REM stage sleep during a sleep period is less than a first threshold, the IMD 104 may adjust the CNS parameter such that the CNS may drive the patient 102 through the other sleep stages toward REM stage sleep to increase the amount of time spent in REM stage sleep. Increasing the amount of time the patient 102 spends in REM stage sleep may increase serotonin production in the patient 102. Increasing serotonin production may alleviate or mitigate depression.

As another example, when the sleep cycle information indicates that an amount of time the patient 102 has spent in stage 3 sleep during a sleep period is less than a second threshold, the IMD 104 may adjust the CNS parameter such that the CNS may drive the patient 102 toward stage 3 sleep (e.g., remaining in stage 3 sleep until the patient 102 has spent an amount of time in stage 3 sleep equal to the second threshold). An amount of time the patient 102 spent in stage 1 sleep may also be compared to a third threshold. An amount of time the patient 102 spent in stage 2 sleep may be compared to a fourth threshold. The first, second, third, and fourth thresholds may correspond to an amount of time, or a portion thereof, that a healthy person may spend in REM stage sleep, stage 3 sleep, stage 1 sleep, and stage 2 sleep, respectively.

Transitions from one sleep stage to another sleep stage may be identified by distinct characteristics associated with each stage of a sleep cycle. For example, stage 1 sleep may be identified based on the presence of hypnic jerks (e.g., involuntary twitching of muscles). The accelerometer 148 may be placed on a limb of the patient 102 to detect body movements associated with hypnic jerks. The sensor data collection system 106 may collect the accelerometer data from the accelerometer 148. The IMD 104 and/or the sensor data collection system 106 may analyze the accelerometer data to determine whether the patient 102 is in stage 1 sleep or has transitioned into stage 1 sleep. A first particular number of occurrences of the hypnic jerks (e.g., a threshold number during a particular time period) may indicate that the patient 102 has transitioned from wakefulness to stage 1 sleep. Consistent occurrences of hypnic jerks may indicate that the patient 102 is in stage 1 sleep.

Stage 2 sleep may be identified based on a decrease in body movements (e.g., a decrease in frequency of body movements, a decrease in frequency of hypnic jerks, and/or absence of hypnic jerks) relative to the body movements in stage 1 sleep, the presence of sleep spindles (e.g., bursts of oscillatory brain activities with frequencies approximately between 12 Hz to 14 Hz and a duration of approximately at least 0.5 second), and/or the presence of relatively stable heart rates. The decrease in body movements may be identified from the accelerometer data and/or EMG data. The accelerometer or EMG sensor 146 may be placed on the torso of the patient 102. Because the presence of hypnic jerks may indicate that the patient 102 is in stage 1 sleep, a period of no registered body movements or a decrease in frequency of body movements following the presence of hypnic jerks may indicate that the patient 102 has transitioned from stage 1 sleep to stage 2 sleep. Snoring may also be an indicator of stage 2 sleep which can be measured by either an accelerometer signal disposed to detect breathing motions, respiration sensor placed on the torso or on the nose, an impedance monitoring unit, a microphone, or a combination thereof.

In addition or alternatively, the EEG sensor 140 may be placed on the head of the patient 102 to detect brain electrical activity of the patient 102. The IMD 104 and/or the sensor data collection system 106 may analyze the EEG data (e.g., the brain electrical activities the patient 102) to determine whether the patient 102 is in stage 2 sleep or has transitioned into stage 2 sleep based on the presence of sleep spindles. A first particular number of occurrences of the sleep spindles may indicate that the patient 102 has transitioned from stage 1 sleep to stage 2 sleep. Consistent occurrences of the sleep spindles may indicate that the patient 102 is in stage 2 sleep.

In addition or alternatively, the ECG sensor 144 may be placed on the torso of the patient 102 (e.g., near the chest of the patient 102) to detect electrical activities of the heart of the patient 102. The IMD 104 and/or the sensor data collection system 106 may analyze the ECG data (e.g., the electrical activities of the heart of the patient 102) to determine whether the patient 102 is in stage 2 sleep or has transitioned into stage 2 sleep. A first particular number of occurrences of orderly ECG patterns (e.g., a threshold number during a particular duration) may indicate that the patient 102 has transitioned from stage 1 sleep to stage 2 sleep. Consistent occurrences of the orderly ECG patterns may indicate that the patient 102 is in stage 2 sleep. Stage 1 sleep and stage 2 sleep are considered light sleep stages.

Stage 3 sleep may be identified based on an increase in body movements relative to the body movements of the patient 102 in stage 2 sleep and/or a decrease in frequency of electrical activities of the brain of the patient 102. The IMD 104 and/or the sensor data collection system 106 may analyze the accelerometer data, the EMG data, and/or the EEG data to determine whether the patient 102 is in stage 3 sleep. The increase in body movements may be identified using the accelerometer data and/or the EMG data. A first particular number of occurrences of increased body movements (e.g., a threshold number during a particular duration) may indicate that the patient 102 has transitioned from stage 2 sleep to stage 3 sleep. Consistent occurrences of the increased body movements relative to the body movements in stage 2 sleep may indicate that the patient 102 is in stage 3 sleep. A first particular number of occurrences of brain electrical activities with a decreased frequency relative to the frequency of brain electrical activities in stage 2 sleep (e.g., 0.5 Hz-2 Hz in stage 3 sleep as compared to 12 Hz-14 Hz in stage 2 sleep) may indicate that the patient 102 has transitioned from stage 2 sleep to stage 3 sleep. Consistent occurrences of brain electrical activities with a decreased frequency relative to the frequency of brain electrical activities in stage 2 sleep may indicate that the patient 102 is in stage 3 sleep. Also, a decrease in snoring from stage 2 sleep may be an indicator of stage 3 sleep. Stage 3 sleep is considered a deep sleep stage.

REM stage sleep may be identified based on an increase in eye movements of the patient 102 relative to the eye movements of the patient 102 in stage 3 and/or a decrease in body movements of the patient 102 relative to the body movements of the patient 102 in stage 3, as detected by electrooculography (EOG) for example. The EOG sensor 142 may be placed near the eyes of the patient 102 to detect the eye movements of the patient 102. The IMD 104 and/or the sensor data collection system 106 may analyze the EOG data and/or the accelerometer data to determine whether the patient 102 is in REM stage sleep. A first particular number of occurrences of eye movements with an increased frequency relative to the eye movements in stage 3 (e.g., a threshold number during a particular duration) may indicate that the patient 102 has transitioned from stage 3 sleep to REM stage sleep. Consistent occurrences of eye movements with an increased frequency relative to the frequency of the eye movements in stage 3 sleep may indicate that the patient 102 is in REM stage sleep. In addition, a decrease in snoring from stage 3 sleep, or the absence of snoring may be an indicator of REM stage sleep. Generally, snoring is more prominent in the light sleep stages (e.g., stage 1 sleep and stage 2 sleep), decreases during deep sleep (e.g., stage 3 sleep), and further decreases and may be absent during REM stage sleep. Exceptions to this snoring pattern may apply to patients with certain disorders (e.g., sleep apnea).

When the patient 102 transitions from a sleep stage to wakefulness, such a transition may be detected based on an increase in heart rate relative to a heart rate of the patient 102 in the sleep stage via the ECG data, an increase in a frequency of the brain electrical activities relative to a frequency of the brain electrical activities of the patient 102 in the sleep stage via the EEG data, and an increase in body movement relative to the body movements of the patient 102 in the sleep stage via the accelerometer data, the EMG data, or a combination thereof. Sleep stage determination sensitivity and specificity may be increased by using multiple sensors. For example, the combination of ECG, EEG, and accelerometer may provide a more accurate indication of a current sleep stage that any one of those sensor types alone.

In a particular embodiment, the sensor data collection system 106 determines the sleep cycle information based on the body parameter data and also determines CNS adjustment data based on the sleep cycle information. The sensor data collection system 106 transmits the CNS adjustment data to the IMD 104. The IMD 104 adjusts one or more CNS parameters based on the CNS adjustment data. In a particular embodiment, the IMD 104 or the sensor data collection system 106 determines information regarding efficacy of a CNS therapy based on a comparison of sleep cycle information of the patient 102 before a CNS therapy and sleep cycle information of the patient 102 during and/or after the CNS therapy. For example, the IMD 104 or the sensor data collection system 106 may compare a first sleep quota of the patient 102 before a CNS therapy to a second sleep quota of the patient 102 after the CNS therapy. As another example, the IMD 104 or the sensor data collection system 106 may compare the second sleep quota to a threshold. The system 100 may improve sleep quality of the patient 102 and may, during sleep, treat depression that the patient 102 suffers from.

Figure 2A:
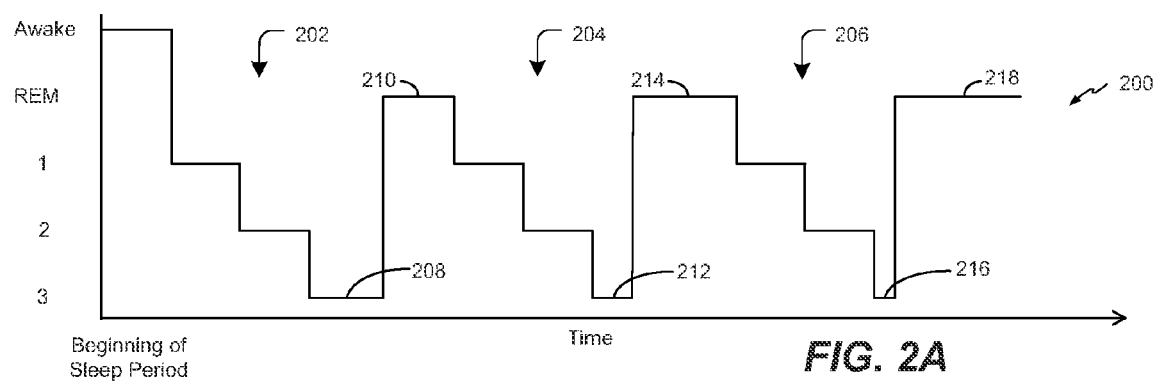
FIG. 2A is a diagram illustrating a sleep pattern when no interference occurs during sleep.

Referring to FIG. 2A, a diagram illustrating a sleep pattern 200 of a patient (e.g., the patient 102 of FIG. 1) with good sleep architecture is shown according to an exemplary embodiment. The sleep pattern 200 may include a first sleep cycle 202, a second sleep cycle 204, and a third sleep cycle 206, each of which are illustrated to scale relative to each other to allow comparison of time periods in FIG. 2A. During the first sleep cycle 202, the patient 102 may spend a first amount of time 208 in stage 3 sleep and may spend a second amount of time 210 in REM stage sleep. During the second sleep cycle 204, the patient 102 may spend a third amount of time 212 in stage 3 sleep and may spend a fourth amount of time 214 in REM stage sleep. The first amount of time 208 is typically a longer duration of time than the third amount of time 212. The second amount of time 210 is typically a shorter duration of time than the fourth amount of time 214. During the third sleep cycle 206, the patient 102 may spend a fifth amount of time 216 in stage 3 sleep and may spend a sixth amount of time 218 in REM stage sleep. The third amount of time 212 is typically a longer duration of time than the fifth amount of time 216. The fourth amount of time 214 is typically a shorter duration of time than the sixth amount of time 218. The sleep pattern 200 may illustrate that an amount of time spent in stage 3 sleep decreases from one sleep cycle to a later sleep cycle as the patient 102 gets closer to completing a sleep period. The sleep pattern 200 may also illustrate that an amount of time spent in REM stage sleep increases from one sleep cycle to a later sleep cycle as the patient 102 gets close to completing the sleep period.

Figure 2B:
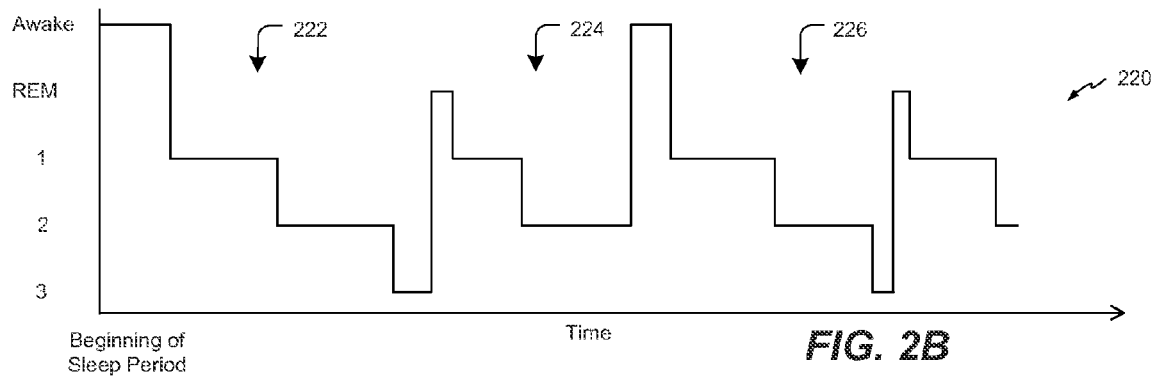
FIG. 2B is a diagram illustrating a sleep pattern when interference occurs during sleep.

Referring to FIG. 2B (which is scaled for comparison to FIG. 2A), a diagram illustrating a sleep pattern 220 of the patient 102 with poor sleep architecture is shown according to an exemplary embodiment. The sleep pattern 220 may include a fourth sleep cycle 222, a fifth sleep cycle 224, and a sixth sleep cycle 226, each of which are illustrated to scale relative to each other to allow comparison of time periods in FIG. 2B. During the fourth sleep cycle 222, the patient 102 spends most of the sleep cycle in light sleep stages 1 and 2 and very little in stage 3 and REM. During the fifth sleep cycle 224, the patient 102 spends the entire cycle in sleep stages 1 and 2 and awakes without achieving stage 3 and REM sleep. During the sixth sleep cycle 226, the patient 102 spends most of the sleep cycle in light sleep stages 1 and 2 and very little in stage 3 and REM sleep before starting the next sleep cycle. The sleep pattern 220 illustrates poor sleep architecture in which the patient is deficient in stage 3 sleep and REM sleep. Deep sleep (e.g., stage 3 sleep) deficiency may result in increased daytime fatigue (among other issues), which may contribute to depression. REM sleep deficiency may decrease serotonin production, which may contribute to and/or cause depression.

Figure 3:
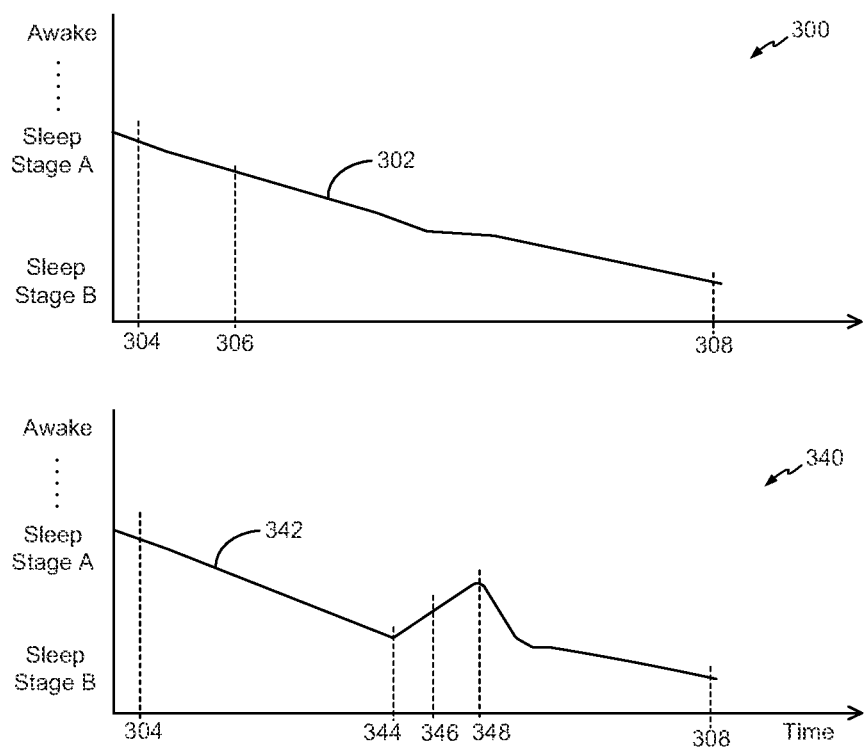
FIG. 3 is a diagram illustrating an effect of cranial nerve stimulation in a sleep stage.

Referring to FIG. 3, a diagram 300 illustrating an effect of cranial nerve stimulation in a sleep stage is shown according to an exemplary embodiment. In diagram 300, the line 302 may represent an amount of time a patient (e.g., the patient 102 of FIG. 1) has spent in a particular sleep stage in a particular sleep cycle (e.g., as monitored by the IMD 104 of FIG. 1 or the sensor data collection system 106). In diagram 300, CNS may be adjusted and applied to help drive the patient from sleep stage A to sleep stage B when the sleep cycle information indicates that the patient is transitioning into Sleep stage A sleep at time 304, indicates that a current sleep stage is sleep stage A, indicates that a predetermined amount of time 306 has been spent in sleep stage A during a sleep cycle, or a combination thereof. The patient may transition to sleep stage B at time 308. In some embodiments, transitioning the patient from one stage to another may improve the patient's sleep architecture, increase the amount of deep sleep, increase the amount of REM sleep, or a combination thereof.

In diagram 340, line 342 represents a patient's stage 2 sleep beginning to transition away from sleep stage B at time 344 (e.g., toward a light sleep stage or an awake state). Based on the sleep cycle information, the IMD 104 of FIG. 1 may identify the transition at time 344, and in response, the IMD 104 may adjust one or more CNS parameters to adjust the CNS applied to the patient 102 or may start applying CNS according to the adjusted one or more CNS parameters, at time 346. The CNS may drive the patient 102 toward sleep stage B. In response to receiving the CNS applied according to the one or more adjusted parameters, the patient 102 may remain or return to sleep stage A at time 348 and continue toward sleep stage B and transition to sleep stage B at time 308.

Figure 4:
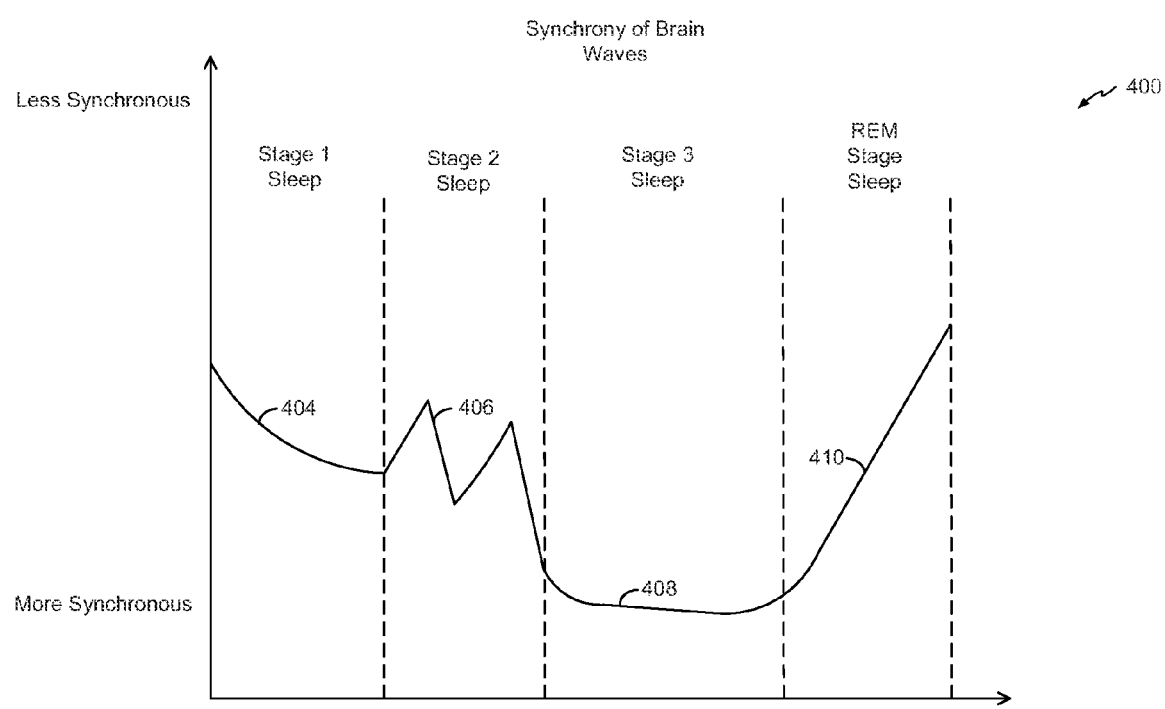
FIG. 4 is a diagram illustrating cranial nerve stimulation parameter adjustments based on sleep cycle information.

Referring to FIG. 4, a diagram 400 illustrating cranial nerve stimulation parameter adjustments based on sleep cycle information is shown according to an exemplary embodiment. The diagram 400 illustrates, in a simplified form, brain wave synchrony over time in various sleep stages. The diagram 400 may be a synchrony profile. The synchrony profile may indicate synchrony level changes in each sleep stage as measured by different EEG channels (e.g., different EEG probes) when no interference occurs during sleep. The diagram 400 may include a first segment 404, a second segment 406, a third segment 408, and a fourth segment 410. Synchrony of the brain waves may include synchrony of brain wave frequency as measured by the different EEG channels, synchrony of brain wave energy as measured by the different EEG channels, synchrony of brain wave stability as measured by the different EEG channels, synchrony of brain wave phase as measured by the different EEG channel, or a combination thereof. In addition, the change in synchrony of brain waves may also be measured within and/or across multiple EEG channels. Furthermore, the change in synchrony within and/or across multiple channels of different body parameters may also be measured.

As shown in FIG. 4, when a patient (e.g., the patient 102 of FIG. 1) is in stage 1 sleep, a synchrony of the brain waves may increase (i.e., become more synchronous) relative to a synchrony of the brain waves when the patient is awake, as indicated by the first segment 404. When the patient is in stage 2 sleep, a synchrony of the brain waves may fluctuate as indicated by the second segment 406. When the patient is in stage 3 sleep, a synchrony of the brain waves may increase relative to the synchrony of the brain waves in stage 2 sleep, as indicated by the third segment 408. When the patient is in REM stage sleep, a synchrony of the brain waves may decrease (i.e., become less synchronous) relative to the synchrony of the brain waves in stage 3 sleep, as indicated by the fourth segment 410.

A medical device (e.g., the IMD 104 of FIG. 1) may monitor brain wave synchrony level changes of the patient 102 based on the sleep cycle information (e.g., the EEG data) to adjust one or more CNS parameters. The one or more CNS parameters may include a pulse width, an output current, a CNS frequency, a CNS duty cycle, a CNS on-time, a CNS off-time, a CNS frequency sweep, burst frequency, or a combination thereof. The one or more CNS parameters may be adjusted such that synchrony of the brain waves may substantially conform to the synchrony profile. For example, when the patient is in stage 2 sleep, the one or more CNS parameters may be adjusted such that synchrony of the brain waves may fluctuate (as in normal stage 2 sleep). As another example, when the patient is in stage 3 sleep, the one or more CNS parameters may be adjusted such that the synchrony may decrease (driving the patient toward REM stage sleep).

One CNS parameter that may be used to affect the synchrony of the brain is frequency of stimulation pulses. For example, higher frequency stimulation pulses (e.g., 100 Hz or more, 100-200 Hz, 100-350 Hz) may have a desynchronizing affect while low frequency stimulation pulses (e.g., 30 Hz or less, 50 Hz or less, less than 100 Hz) may have a synchronizing effect. Therefore, low frequency stimulation pulses may be used to drive the patient from stage 1 sleep to stage 2 sleep and from stage 2 sleep to stage 3 sleep while higher frequency stimulation pulses may be used to drive the patient from stage 3 sleep to REM stage sleep. As another example, CNS may be vagus nerve stimulation (VNS) to stimulate the vagus nerve. Conventional VNS (e.g., pulse frequency of about 30 Hz, pulse width around 250-500 microseconds, on-time of about 30 sec, and an off-time of 5 minutes) may be used to drive the patient from stage 1 sleep to stage 2 sleep and from stage 2 sleep to stage 3 sleep. Microburst VNS (e.g., pulse frequency of about 100-250 Hz, pulse width around 250-500 microseconds, 2-10 pulses per burst, an interburst interval of about 100 milliseconds to 1 second, a burst duration of 100 milliseconds or less) may be used to drive the patient from stage 3 sleep to REM stage sleep. Other stimulation parameters may be used in conjunction with, or instead of frequency, to affect synchrony of the brain. In some embodiments, one or more signal parameters may become more or less randomized to affect the synchrony of the brain. For example, pulse width, pulse amplitude, frequency, duty cycle, on-time, off-time, or a combination thereof may be randomized within a range to desynchronize the brain. The range of randomization, the number on parameters randomized, or a combination thereof may increase to further desynchronize the brain.

Figure 5A:
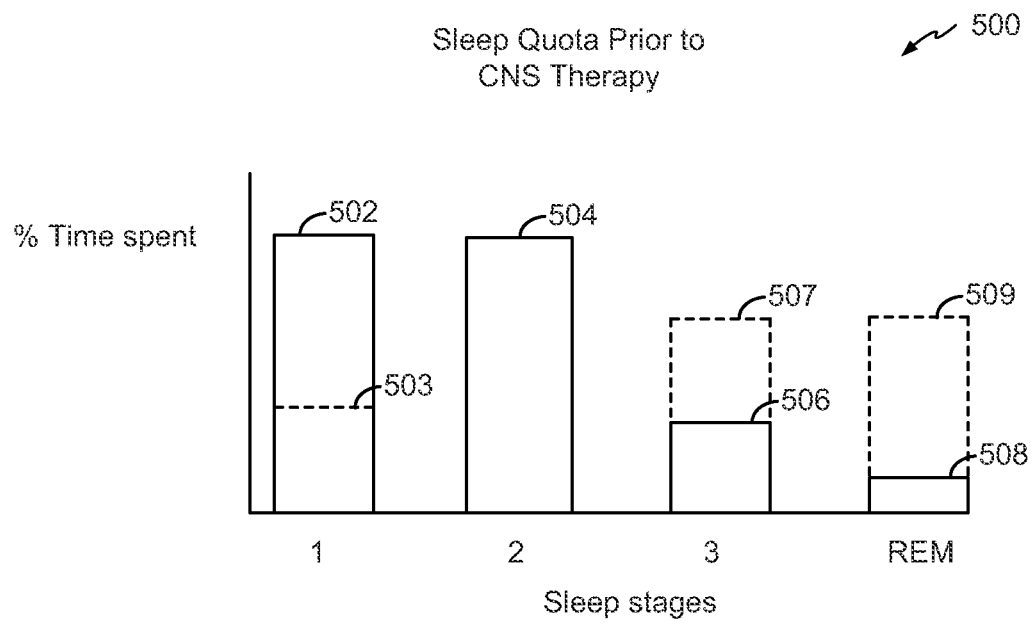
FIG. 5A is a diagram of a sleep quota of a patient before receiving cranial nerve stimulation.

Referring to FIG. 5A, a diagram of a first sleep quota 500 of a patient (e.g., the patient 102 of FIG. 1) before receiving CNS therapy to treat depression is shown according to an exemplary embodiment. The first sleep quota 500 may include a first portion 502, a second portion 504, a third portion 506, and a fourth portion 508. The first sleep quota 500 may be a sleep quota of the patient with poor sleep architecture. The first portion 502 may correspond to an accumulative amount of time the patient spent in stage 1 sleep in a first sleep period (e.g., a night) before receiving the CNS therapy. The first sleep period may include one or more sleep cycles. Portion 503 represents an approximate amount of time a patient with good sleep architecture would spend in stage 1 sleep. The second portion 504 may correspond to an accumulative amount of time the patient spent in stage 2 sleep in the first sleep period. The third portion 506 may correspond to an accumulative amount of time the patient spent in stage 3 sleep in the first sleep period. Portion 507 represents an approximate amount of time a patient with good sleep architecture would spend in stage 3 sleep. The fourth portion 508 may correspond to an accumulative amount of time the patient spent in REM stage sleep in the first sleep period. Portion 509 represents an approximate amount of time a patient with good sleep architecture would spend in REM stage sleep. The diagram indicates that the patient spends far too little time in REM stage sleep, which may result in reduce serotonin production, which may contribute to and/or cause depression. The diagram also indicates that the patient spends too little time in stage 3 sleep (e.g., deep sleep), which may result in increased daytime fatigue (among other issues) and may contribute to depression.

In some embodiments, the medical device (e.g., the IMD 104 of FIG. 1) may use the sleep quota information to adjust CNS. For example, the medical device may adjust stimulation based on the amount of time spent in REM stage sleep. If the patient is not getting enough REM stage sleep, the medical device may be configured to adjust CNS parameters to drive the patient towards REM stage sleep when a transition is detected from one sleep stage to another, based on a current sleep stage, when a particular amount of time has passed in the current sleep stage, based on one or more thresholds associated with one or more sleep stages (e.g., minimum amount of time that should be spent in a particular sleep stage or a fraction thereof), or a combination thereof. As the amount of REM stage sleep changes, the CNS parameters may be adjusted to promote the appropriate amount of REM stage sleep. As an example of using CNS to increase the amount of time spent in REM stage sleep, the medical device, using sleep quota 500, may apply synchronizing stimulation after stage 1 sleep is detected to drive the patient toward stage 2 sleep and reduce the amount of time spent in stage 1 sleep. The medical device may continue to apply or resume the application of synchronizing stimulation during stage 2 sleep (e.g., certain parameters may be adjusted specific to stage 2 sleep) to drive the patient toward stage 3 sleep. During stage 3 sleep, the medical device may continue to apply or resume the application of synchronizing stimulation to keep the patient in stage 3 sleep for a particular amount of time (e.g., certain parameters may be adjusted specific to stage 3 sleep), after which the stimulation may change, or transition, to a desynchronizing stimulation to drive the patient toward REM stage sleep. Once the patient is in REM stage sleep, the stimulation may continue or resume as a desynchronizing stimulation, switch between synchronizing and desynchronizing stimulation, adjust to synchronizing stimulation, or discontinue stimulation until the next sleep cycle.

Figure 5B:
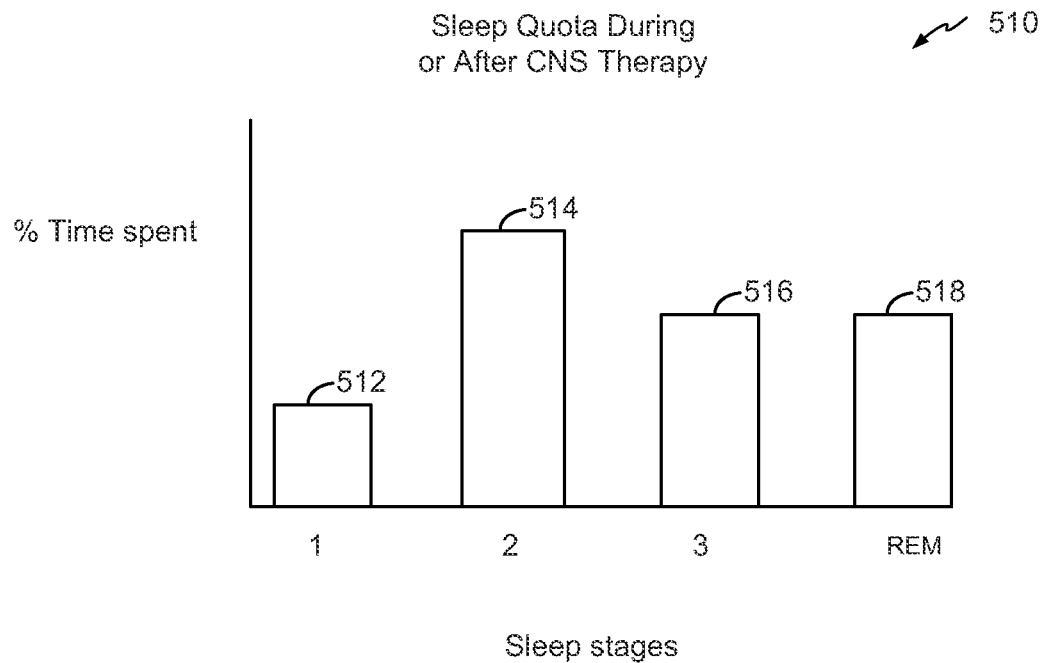
FIG. 5B is a diagram of a sleep quota of the patient of FIG. 5A after receiving cranial nerve stimulation.

Referring to FIG. 5B (illustrated in a scale comparable to FIG. 5A), a diagram of a second sleep quota 510 of the patient of FIG. 5A after receiving the CNS therapy to treat depression is shown according to an exemplary embodiment. The second sleep quota 510 may include a fifth portion 512, a sixth portion 514, a seventh portion 516, and an eighth portion 518. The fifth portion 512 may correspond to an accumulative amount of time the patient spent in stage 1 sleep in a second sleep period (e.g., a night) during the CNS therapy or after the CNS therapy (while recovering). The second sleep period may include multiple sleep cycles. The sixth portion 514 may correspond to an accumulative amount of time the patient spent in stage 2 sleep in the second sleep period. The third portion 516 may correspond to an accumulative amount of time the patient spent in stage 3 sleep in the second sleep period. The fourth portion 518 may correspond to an accumulative amount of time the patient spent in REM stage sleep in the second sleep period.

Information regarding efficacy of the CNS therapy may be determined based on a comparison of the first sleep quota 500 to the second sleep quota 510 (e.g., via the IMD 104 of FIG. 1). A result of the comparison may indicate that the seventh portion 516 is greater than the third portion 506 and the eighth portion 518 is greater than the fourth portion 508. Thus, the comparison may indicate that the patient spends more time in stage 3 sleep and REM stage sleep during or after the CNS therapy. The increase of time the patient spends in stage 3 sleep and REM stage sleep may indicate that the CNS is effective in treating a particular disorder. For example, when the CNS therapy is to treat depression, the comparison may indicate that the CNS therapy is effective in treating depression as an increase in REM stage sleep may increase the serotonin production in the patient. Increased serotonin production may alleviate or mitigate depression. In a particular embodiment, the first sleep quota 500 and/or the second sleep quota 510 may be compared to a threshold to determine a degree of efficacy. For example, a threshold of REM stage sleep may correspond to a particular amount of time that a healthy person spends in REM stage sleep in a sleep cycle and/or a sleep period. The fourth portion 508 and the eighth portion 518 may be compared to the threshold to determine an amount of improvement (e.g., how much more time the patient spends in REM stage sleep) as a measure of the efficacy.

The information regarding efficacy of the CNS therapy and/or the degree of efficacy may be determined by the IMD 104 of FIG. 1, the sensor data collection system 106, the external programming device 108, the external computing device 160, or a combination thereof. The IMD 104, the sensor data collection system 106, the external programming device 108, the external computing device 160, or a combination thereof, may adjust or generate a recommendation (e.g., via a report) regarding adjustments that can be made to improve the efficacy based on the information regarding efficacy of the CNS therapy and/or the degree of efficacy.

The IMD 104, the sensor data collection system 106, the external programming device 108, the external computing device 160, or a combination thereof, may communicate the information regarding efficacy of the CNS therapy and/or the degree of efficacy to the patient, to a health care provider, or a combination thereof. For example, the IMD 104, the sensor data collection system 106, the external programming device 108, the external computing device 160, or a combination thereof, may generate a report that includes the information regarding efficacy of the CNS therapy and/or the degree of efficacy, may show the information regarding efficacy of the CNS therapy and/or the degree of efficacy via a display, etc. The IMD 104, the sensor data collection system 106, the external programming device 108, the external computing device 160, or a combination thereof, may adjust one or more CNS parameters based on the information regarding the efficacy of the CNS therapy and/or the degree of efficacy.

Figure 6:
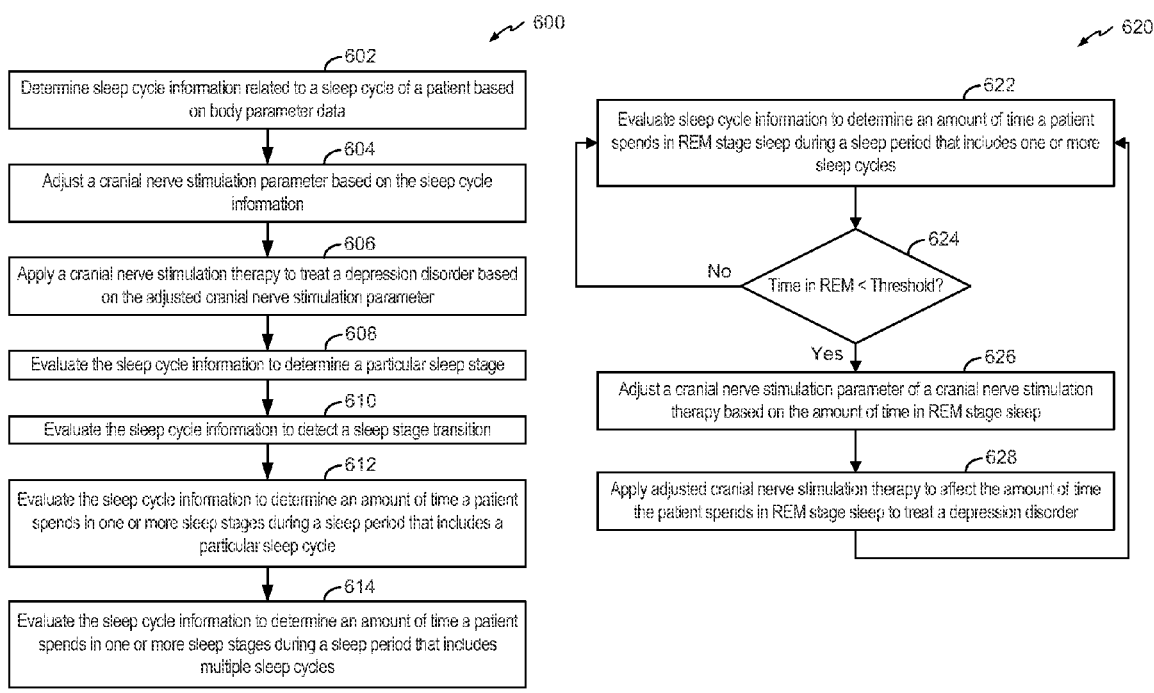
FIG. 6 is a flow chart of a first particular embodiment of a method of operation of a medical device associated with a cranial nerve stimulation therapy to treat depression during sleep.

Referring to FIG. 6, a flow chart of a method 600 of operation of a medical device, such as the IMD 104 of FIG. 1, the sensor data collection system 106, the external programming device 108, the external computing device 160, or a combination thereof, associated with a cranial nerve stimulation therapy to treat depression during sleep is shown according to an exemplary embodiment. The method 600 includes determining sleep cycle information related to a sleep cycle of a patient based on body parameter data, at 602. For example, referring to FIG. 1, based on the body parameter data, the IMD 104 may determine sleep cycle information related to a sleep cycle of the patient 102. The method 600 may also include adjusting a cranial nerve stimulation parameter based on the sleep cycle information, at 604. For example, referring to FIG. 1, based on the sleep cycle information, the IMD 104 may adjust one or more CNS parameters to adjust the CNS applied to the patient 102. The one or more CNS parameters may include a pulse width, an output current, a CNS frequency, a CNS duty cycle, a particular nerve or nerves stimulated, a CNS frequency sweep, CNS on-time, CNS off-time, a CNS burst stimulation, or a combination thereof. As another example, referring to FIG. 4, the IMD 104 may also, or in the alternative, affect a synchrony of brain waves by adjusting the one or more CNS parameters to drive the patient through each stage of a sleep cycle or from one sleep stage to another.

The method 600 further includes applying a cranial nerve stimulation therapy to treat depression based on the adjusted cranial nerve stimulation parameter, at 606. For example, referring to FIG. 1, the IMD 104, the sensor data collection system 106, the external programming device 108, the external computing device 160, or a combination thereof, may adjust one or more CNS parameters to adjust the CNS applied to the patient 102. The one or more CNS parameters may be used to generate stimulation signals applied to a cranial nerve of the patient 102.

In a particular embodiment, the method 600 further includes evaluating the sleep cycle information to determine a particular sleep stage, at 608. For example, referring to FIG. 1, the IMD 104, the sensor data collection system 106, the external programming device 108, the external computing device 160, or a combination thereof, may evaluate the sleep cycle information to determine a sleep stage of the patient. In a particular embodiment, the method 600 further includes evaluating the sleep cycle information to detect a sleep stage transition, at 610. For example, referring to FIG. 1, the IMD 104, the sensor data collection system 106, the external programming device 108, the external computing device 160, or a combination thereof, may evaluate the sleep cycle information to detect a sleep stage transition.

In a particular embodiment, the method 600 further includes evaluating the sleep cycle information to determine an amount of time the patient spends in one or more sleep stages during a particular sleep cycle, at 612. For example, referring to FIG. 1, the IMD 104, the sensor data collection system 106, the external programming device 108, the external computing device 160, or a combination thereof, may evaluate the sleep cycle information to determine an amount of time the patient 102 spends in one or more sleep stages during a particular sleep cycle. In a particular embodiment, the method 600 further includes evaluating the sleep cycle information to determine an amount of time the patient spends in one or more sleep stages during a sleep period that includes multiple sleep cycles, at 614. For example, referring to FIG. 1, the IMD 104, the sensor data collection system 106, the external programming device 108, the external computing device 160, or a combination thereof, may evaluate the sleep cycle information to an amount of time the patient 102 spends in one or more sleep stages during a sleep period that includes multiple sleep cycles.

Thus, the method 600 may enable a medical device to gather and monitor patient information through each stage of a sleep cycle. Completing a sleep cycle may improve sleep quality of the patient and may increase production of serotonin in the patient.

Referring again to FIG. 6, a flow chart of a method 620 of operation of a medical device, such as the IMD 104 of FIG. 1, associated with a cranial nerve stimulation therapy is shown according to an exemplary embodiment. The method 620 includes evaluating sleep cycle information to determine an amount of time a patient spends in REM stage sleep during a sleep period that includes one or more sleep cycles, at 622. The method 620 may also include determining whether the amount of time spent in REM stage sleep is less than a threshold, at 624. The threshold may be set by the user (e.g., patient, physician, or healthcare provider) and may be adjusted based on the patient's response to stimulation or for any other reason. The method 620 may also include adjusting a cranial nerve stimulation parameter of a cranial nerve stimulation therapy based on the amount of time in REM stage sleep, at 626. If the amount of time in REM stage sleep is only slightly below the threshold, slight adjustments to the therapy may be made to one or more cranial nerve stimulation parameters. If the amount of time in REM stage sleep is far below the threshold, more dramatic adjustments may need to be made to the one or more cranial nerve stimulation parameters. The adjusted cranial nerve stimulation parameters may be selected to drive the patient through one or more sleep stages (e.g., stage 1 sleep, stage 2 sleep, and stage 3 sleep) toward REM stage sleep. After the cranial nerve stimulation parameter is adjusted, the method 620 may further include applying the adjusted cranial nerve stimulation therapy (e.g., where the cranial nerve may be the vagus nerve, trigeminal nerve, hypoglossal nerve, glossopharyngeal nerve, or a combination thereof) to affect the amount of time the patient spends in REM stage sleep to treat a depression disorder, at 628. For example, the adjusted stimulation may move the patient toward REM stage sleep. After applying the adjusted stimulation therapy, the method 620 may return to 622 and begin the method 620 again to further adapt or adjust to changes in the amount of REM stage sleep resulting from the adjusted cranial nerve stimulation therapy. The synchrony of brain waves may be affected by adjusting the one or more CNS parameters to drive the patient from light sleep to deep sleep and from deep sleep to REM. Driving the patient in and/or through the sleep stages may improve the patient's sleep architecture and neurologic condition. For example, applying CNS with parameters adjusted based on the amount of time spent in REM stage sleep may increase the amount of time spent in REM state sleep, which may increase production of serotonin in the patient and alleviate/lessen the patient's depression.

Figure 7:
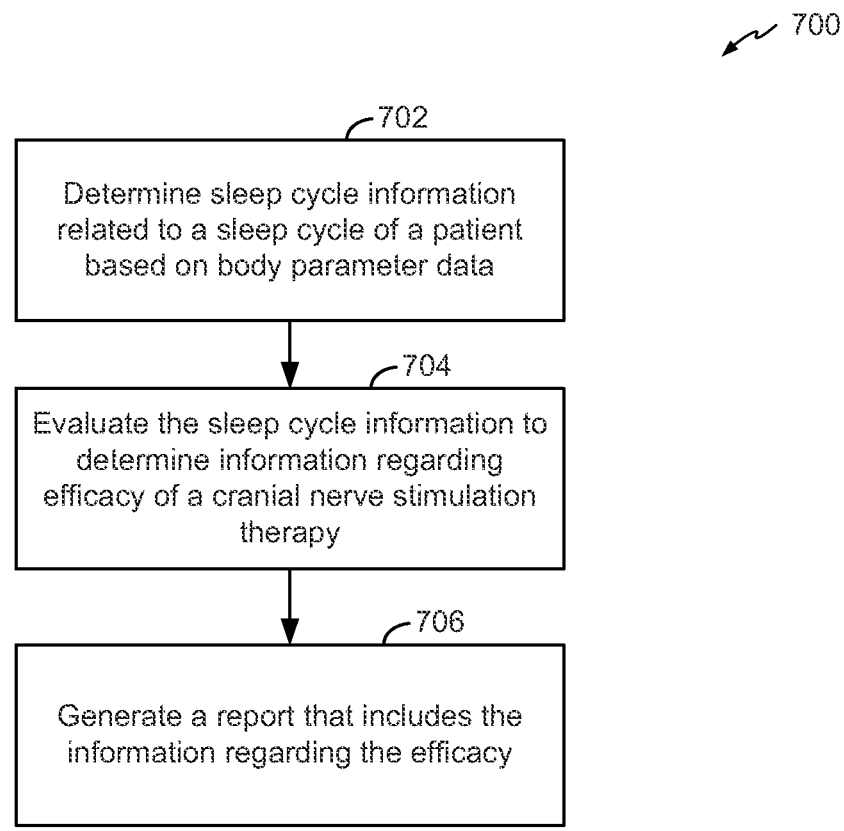
FIG. 7 is a flow chart of a second particular embodiment of a method of operation of a medical device associated with a cranial nerve stimulation therapy to treat depression during sleep.

FIG. 7 is a flow chart of a second particular embodiment of a method of operation of a medical device, such as the IMD 104 of FIG. 1, the sensor data collection system 106, the external programming device 108, the external computing device 160, or a combination thereof, associated with a cranial nerve stimulation therapy to treat depression during sleep according to an exemplary embodiment. The method 700 includes determining sleep cycle information related to a sleep cycle of a patient based on body parameter data, at 702. For example, referring to FIG. 1, based on the body parameter data, the IMD 104 may determine sleep cycle information related to a sleep cycle of the patient 102. The method 700 also includes evaluating the sleep cycle information to determine information regarding efficacy of a cranial nerve stimulation therapy, at 704. For example, referring to FIG. 5, the information regarding efficacy of the CNS therapy may be determined based on a comparison of the first sleep quota 500 to the second sleep quota 510. As another example, the efficacy may be determined based on the comparison of the amount of time spent in REM stage sleep before cranial nerve stimulation therapy and the amount of time spent in REM stage sleep after or during cranial nerve stage therapy. The method 700 further includes generating a report that includes the information regarding efficacy, at 706. For example, referring to FIG. 5, the IMD 104, the sensor data collection system 106, the external programming device 108, the external computing device 160, or a combination thereof, may generate a report that includes information regarding efficacy of the CNS therapy and/or the degree of efficacy. Thus, the method 700 may enable determination of information regarding efficacy of a therapy. Determining efficacy of a therapy may enable adjustment of the therapy to improve the efficacy.

Although the description above contains many specificities, these specificities are utilized to illustrate some of the exemplary embodiments of this disclosure and should not be construed as limiting the scope of the disclosure. The scope of this disclosure should be determined by the claims, their legal equivalents. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one.

The disclosure is described above with reference to drawings. These drawings illustrate certain details of specific embodiments that implement the systems and methods of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising computer readable storage device, or machine-readable media for carrying, or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing descriptions of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
    determining, at a computing device, sleep cycle information associated with a sleep cycle of a patient based on body parameter data;
    adjusting, at the computing device, a cranial nerve stimulation parameter based on the sleep cycle information, wherein the sleep cycle information includes an amount of time the patient has spent in a particular sleep stage; and
    treating depression in the patient by initiating application of a cranial nerve stimulation therapy to the patient based on the adjusted cranial nerve stimulation parameter.

2. The method of claim 1, wherein the body parameter data comprises at least one of electroencephalography (EEG) data, electrooculography (EOG) data, electromyography (EMG) data, electrocardiography (ECG) data, respiration data, or accelerometer data.

3. The method of claim 1, wherein the sleep cycle information further includes one of a sleep stage transition, an amount of time the patient has spent in one or more sleep stages during a particular sleep cycle, or an amount of time the patient has spent in the one or more sleep stages during a sleep period that includes multiple sleep cycles.

4. The method of claim 1, further comprising receiving the body parameter data from a sensor monitoring the patient.

5. The method of claim 1, further comprising:
determining efficacy information of the cranial nerve stimulation therapy based on the sleep cycle information;
determining a second adjusted cranial nerve stimulation parameter based on the efficacy information; and
adjusting the cranial nerve stimulation therapy based on the second adjusted cranial nerve stimulation parameter.

6. The method of claim 5, further comprising:
generating a report that includes the efficacy information, the second adjusted cranial nerve stimulation parameter, or a combination thereof; and
communicating the report to at least one of the patient or a health care provider.

7. The method of claim 1, wherein the sleep cycle information further includes an amount of time the patient spent in a rapid eye movement (REM) stage sleep during a sleep period that includes one or more sleep cycles, and when the amount of time the patient has spent in the REM stage sleep is less than a threshold, the cranial nerve stimulation parameter is adjusted to apply the cranial nerve stimulation therapy to decrease brain synchrony.

8. The method of claim 1, wherein the cranial nerve stimulation therapy is applied to a vagus nerve, a trigeminal nerve, a hypoglossal nerve, a glossopharyngeal nerve, or a combination thereof, of the patient such that synchrony of a brain of the patient substantially conforms to a synchrony profile, and wherein the sleep cycle information further includes the particular sleep stage of the patient.

9. The method of claim 1, wherein the cranial nerve stimulation parameter includes at least one of a pulse width, an output current, a cranial nerve stimulation frequency, a cranial nerve stimulation duty cycle, a particular nerve or nerves stimulated, a cranial nerve stimulation frequency sweep, a cranial nerve stimulation on-time, or a cranial nerve stimulation off-time.

10. A device comprising:
a processor configured to:
determine sleep cycle information associated with a sleep cycle of a patient based on body parameter data; and
adjust a cranial nerve stimulation parameter based on the sleep cycle information, wherein the sleep cycle information includes an amount of time the patient has spent in a particular sleep stage;
a memory coupled to the processor; and
a therapy delivery unit configured to apply a cranial nerve stimulation therapy to treat depression in the patient based on the adjusted cranial nerve stimulation parameter.

11. The device of claim 10, wherein the processor is further configured to:
determine efficacy information of the cranial nerve stimulation therapy; and
communicate the efficacy information of the cranial nerve stimulation therapy to a health care provider, the patient, or a combination thereof.

12. The device of claim 11, wherein the efficacy information of the cranial nerve stimulation therapy is determined based on a comparison of the sleep cycle information to second sleep cycle information of the patient prior to receiving the cranial nerve stimulation therapy.

13. The device of claim 11, wherein the efficacy information of the cranial nerve stimulation therapy is determined based on a comparison of an amount of time the patient has spent in rapid eye movement (REM) stage sleep to a threshold.

14. The device of claim 10, further comprising a transceiver coupled to the processor, the transceiver configured to communicate with a sensor data gathering unit to receive the body parameter data from a sensor that is attached to the patient.

15. The device of claim 11, wherein the processor is further configured to adjust the adjusted cranial nerve stimulation parameter based on the efficacy information.

16. A non-transitory computer-readable medium comprising instructions executable by a processor to:
determine sleep cycle information associated with a sleep cycle of a patient based on body parameter data;
adjust a cranial nerve stimulation parameter based on the sleep cycle information, wherein the sleep cycle information includes an amount of time the patient has spent in a particular sleep stage; and
treat depression in the patient by initiating application of a cranial nerve stimulation therapy to the patient based on the adjusted cranial nerve stimulation parameter.

17. The non-transitory computer-readable medium of claim 16, wherein the cranial nerve stimulation therapy comprises a microburst cranial nerve stimulation therapy.

18. The non-transitory computer-readable medium of claim 17, wherein the adjusted cranial nerve stimulation parameter includes at least one a cranial nerve stimulation frequency between 100 hertz (Hz) and 250 Hz, a pulse width between 250 microseconds and 500 microseconds, pulses per burst between 2 and 10, an interburst interval of 100 milliseconds to 1 second, or a burst duration of 100 milliseconds.

19. The method of claim 1, wherein the adjusted cranial nerve stimulation parameter includes a cranial nerve stimulation frequency less than 100 hertz (Hz) when transitioning the patient from stage 1 sleep into stage 2 sleep or from stage 2 sleep into stage 3 sleep.

20. The method of claim 1, wherein the adjusted cranial nerve stimulation parameter includes a cranial nerve stimulation frequency greater than or equal to 100 hertz (Hz) when transitioning the patient from stage 3 sleep into rapid eye movement (REM) stage sleep.

* * * * *